(12) United States Patent
Dong et al.

(10) Patent No.: US 9,018,449 B2
(45) Date of Patent: Apr. 28, 2015

(54) **TRANSFORMATION METHODS FOR GUAYULE USING *AGROBACTERIUM* AND REDUCED LIGHT TO SLOW METABOLISM AND ENHANCE RECOVERY**

(75) Inventors: Niu Dong, Albany, CA (US); Katrina Cornish, Pinole, CA (US)

(73) Assignee: The United States of America, represented by The Secretary of Agiculture, Washington, DC (US)

( * ) Notice: Subject to any disclaimer, the term of this patent is extended or adjusted under 35 U.S.C. 154(b) by 1529 days.

(21) Appl. No.: 10/797,346

(22) Filed: Mar. 10, 2004

(65) Prior Publication Data

US 2006/0218660 A1 Sep. 28, 2006

(51) Int. Cl.
*A01H 1/00* (2006.01)
*C12N 15/82* (2006.01)

(52) U.S. Cl.
CPC .................. *C12N 15/8205* (2013.01)

(58) Field of Classification Search
USPC ....................................................... 800/294
See application file for complete search history.

(56) References Cited

U.S. PATENT DOCUMENTS

| | | | | |
|---|---|---|---|---|
| 4,363,188 A | * | 12/1982 | Dastoor et al. | 435/430.1 |
| 4,983,729 A | * | 1/1991 | Sikora | 435/166 |
| 5,180,873 A | * | 1/1993 | Jorgensen | 800/266 |
| 5,580,942 A | | 12/1996 | Cornish | |
| 5,633,433 A | * | 5/1997 | Backhaus et al. | 800/295 |
| 5,717,050 A | | 2/1998 | Cornish | |
| 6,645,747 B1 | | 11/2003 | Hallahan et al. | |
| 2006/0218660 A1 | * | 9/2006 | Dong et al. | 800/278 |

OTHER PUBLICATIONS

Dong, N., Cornish, K. 2003 Transformation of guayule leaf sections. Association for the Advancement of Industrial Crops Conference. p. 26 published Oct. 12, 2003.*
Dong, N. et al. Low light and low ammonium are key factors for gusyule leaf tissue shoot organogenesis and transformation. Plant Cell. Rep. (2006) 25: 26-34. Published online Oct. 25, 2005.*
Anonymous. Gardenaction. "How to care for Strawberries." available at:http://www.gardenaction.co.uk/fruit_veg_diary/fruit_veg_mini_project_february_2_strawberry2.asp accessed Mar. 14, 2011.*
Anonymous. Definition of "Plantlet" from Merriam-Webster Dictionary. Available at: http://www.merriam-webster.com/dictionary/plantlet accessed Mar. 14, 2011.*
Castillon et al. "A simplified Protocol for Micropropagation of Guayule (*Parthenium agrentatum* Gray)." In Vitro Cell. Dev. Biol.—Plant 36:215-219 May-Jun. 2000.*
Anonymous. Tissue Culture Laboratory. 1.1 Micropropagation Unit. Tissue Culture CIP training manual. available at: http://www.cipotato.org/csd/materials/Tissue/Capitulo1.pdf accessed Mar. 14, 2011.*
Wood, Marcia. "Allergic to Rubber?" Agricultural Research May 1999 vol. 47, No. 5 pp. 18-20.*
Thomas, John C. et al. "Light-induced expression of ipt from *Agrobacterium tumefaciens* results in cytokinin accumulation and osmotic stress symptoms in transgenic tobacco." Plant Molecular Biology 27: 225-235 1995.*
Zavala, M.E., Biesboer, D.D., and Mahlberg, P.G., "Callus Induction and Organogenesis in Cultured Tissues of *Parthenium argentatum*," (1982) *Phytomorphology* 32(4):340-344.
Trautmann, I.A., and Visser, J.H., "An in vitro study of organogenesis in guayule (*Parthenium argentatum* Gray)," (1990) *Plant Science* 72:275-281.
Pan, Z., Ho, J., Feng, Q., Huang, D-S., and Backhaus, R.A., "*Agrobacterium*—mediated transformation and regeneration of guayule," (1996) *Plant Cell, Tissue and Organ Culture* 46:143-150.
Pellegrineschi, A., "In vitro plant regeneration via organogenesis of cowpea [*Vigna unguiculata* (L.) Walp.]," (1997) *Plant Cell Reports* 17:89-95.

* cited by examiner

*Primary Examiner* — Annette Para
(74) *Attorney, Agent, or Firm* — John D. Fado; Howard V. Owens, Jr.

(57) ABSTRACT

This invention is directed to a new technique of genetic transformation using low light conditions and leaf strips in the Guayule plant, *Parthenium argentatum*. The invention also relates to new lines of Guayule, created through this technique.

6 Claims, 6 Drawing Sheets

1/2MSBN

| | |
|---|---|
| CAISSON MS Salts | 2.17 g |
| BA | 0.2 mg |
| NAA | 2.0 mg |
| Sucrose | 15 g |
| pH | 5.8 |
| Agar | 8 g |

*********autoclave*********
*Add*

| | |
|---|---|
| B5 Vitamin | 1 ml |

1/10MSBN

| | |
|---|---|
| CAISSON MS Salts | 0.433 g |
| BA | 2 mg |
| NAA | 0.5 mg |
| glucose | 10 g |
| MES | 100 mg |
| pH | 5.4 |
| (For solid, add Gellan Gum | 7 g) |

*********autoclave*********
*Add*

| | |
|---|---|
| B5 Vitamin | 1 ml |
| Acetosyringon | 1 ml |
| Pluronic F68 (10%) | 5 ml |

1/2MSB2G1

| | |
|---|---|
| CAISSON MS Salts | 2.17 g |
| $KNO_3$ | 5 g |
| BA | 2 mg |
| Sucrose | 30 g |
| pH | 5.8 |
| Agar | 8 g |

*********autoclave*********
*Add*

| | |
|---|---|
| B5 Vitamin | 1 ml |
| $CaCl_2$ (2.5M) | 1 ml |
| $MgSO_4$ (1 M) | 2 ml |
| Timentin | 200 mg |
| Glufosinate (50 mg/ml) | 20 µl |

1/2MSB1G0.6

| | |
|---|---|
| CAISSON MS Salts | 2.17 g |
| $KNO_3$ | 5 g |
| BA | 1 mg |
| Sucrose | 30 g |
| pH | 5.8 |
| Agar | 8 g |

*********autoclave*********
*Add*

| | |
|---|---|
| B5 Vitamin | 1 ml |
| $CaCl_2$ (2.5M) | 1 ml |
| $MgSO_4$ (1 M) | 2 ml |
| Timentin | 100 mg |
| Glufosinate (50 mg/ml) | 12 µl |

RootG0.5

| | |
|---|---|
| CAISSON MS Salts | 2.17 g |
| IBA | 0.1 mg |
| Sucrose | 15 g |
| pH | 5.8 |
| Agar | 8 g |

*********autoclave*********
*Add*

| | |
|---|---|
| B5 Vitamin | 1 ml |
| Timentin | 100 mg |
| Glufosinate (50 mg/ml) | 10 µl |

1/2MS

| | |
|---|---|
| CAISSON MS Salts | 2.17 g |
| Sucrose | 15 g |
| pH | 5.8 |
| Agar | 8 g |

*********autoclave*********
*Add*

| | |
|---|---|
| B5 Vitamin | 1 ml |

FIG. 6

TRANSFORMATION METHODS FOR GUAYULE USING *AGROBACTERIUM* AND REDUCED LIGHT TO SLOW METABOLISM AND ENHANCE RECOVERY

BACKGROUND OF THE INVENTION

1. Field of the Invention

The present invention relates to the transformation of the Guayule plant, *Parthenium argentatum*.

2. Description of the Art

Natural rubber is a strategic raw material. Approximately 40,000 different products, to include at least 400 different medical devices, require natural rubber. Modern aircraft tires, for example, are not manufactured without natural rubber. Synthetic rubber can be made, but it is an imperfect substitute. The difference is apparently due to natural proteins and certain biological catalysts that occur in natural rubber, but which have not yet been reproduced in a synthetic version. Natural rubber, therefore, is of significant economic importance and having an uninterrupted supply of rubber is critical to the nation's economy. Moreover, as the industrial capacity of developing countries continues to build, the demand for natural rubber builds with it.

Natural rubber is a hydrocarbon polymer of cis-1,4-polyisoprene with 400-50,000 isoprene monomeric units enzymatically linked in a head-to-tail configuration. This head-to-tail configuration is apparently critical to the properties of natural rubber, and something that is not reliably reproduced in the synthetics.

Traditionally, virtually all natural rubber used to manufacture products has come from the *Hevea brasiliensis* plant which is native to tropical areas outside the continental United States. At the present time, most *Hevea* production is occurring in parts of the world whose political or economic stability is in question. This has implications for the rubber industry—a steady and predictable supply of rubber cannot be guaranteed from foreign sources. Moreover, because rubber production is currently overseas, shipping costs are a significant factor for users of rubber in the United States.

Many plant species other than *Hevea* produce rubber, although not in equal quality or in a form that is easily harvested. These plants include, but are not limited to, *Euphorbia tirucalli, Taraxacum Kok-saghyz* (Russian dandelion), *Cryosothamnus nauseosus* (rabbit brush), *Asclepias incarnate, Soldiago altissima, Cryptostegia grandiflora* (rubbervine), *Sonchus arvensis, Cacalia atriplicifolia, Ficus elastica* (Indian rubber tree), and *Parthenium argentatum* (Guayule).

Guayule is a particularly promising candidate for the rubber industry in North America because it is native to the Chihuahuan desert of Texas and Mexico, and because the rubber harvested from it shows unusual hypoallergenic properties. Having a local supply of rubber for manufacturers and consumers in North America, therefore, is a quite positive economic development. No longer will the domestic rubber industry be dependent on foreign sources of rubber, often from countries that may not always be dependable in terms of providing a steady source of rubber to manufacturers in the United States.

Moreover, the fact that rubber from Guayule can be used to produce hypoallergenic latex is especially significant. Rubber or latex allergy is a significant problem that affects individuals in many different groups such as health care workers, those who work in laboratories, medical and dental patients, food-service workers, and anyone else who desires the safety and convenience of rubber gloves or appliances. Latex itself is a suspension of rubber particles in aqueous media, and considerable efforts have been expended to isolate and extract latex from various sources.

Extraction of latex rubber from Guayule has previously been described by Cornish in U.S. Pat. No. 5,590,942 (1996) and U.S. Pat. No. 5,717,050 (1998), both entitled Hypoallergenic Natural Rubber Products from *Parthenium argentatum* (Gray) and other non-*Hevea brasiliensis* Species. These patents describe isolation and purification procedures, and also provide considerable background information regarding the need for hypoallergenic latex.

Producing hypoallergenic latex from plants that can be grown within the climate zones of the continental United States is highly desirable and economically quite important. Perfecting the techniques for growing Guayule and increasing the latex-yield per plant is critical to industrial-level production. Central to this process is the transformation of Guayule lines, or the introduction of various genes into the Guayule plant that will operate to boost latex yield, increase its hardiness, or expand its range.

Transformation of Guayule is dependent on a reliable regeneration system. The most common regeneration system that has been used thus far involves shoot node inoculation by *Agrobacterium tumefaciens* which has a low efficiency rate, is enormously time consuming, labor intensive, tedious, and therefore not very practical.

The most highly-refined technique using the shoot node culture system is apparently that described in Pan et al. (1996) which uses a *Agrobacterium tumefaciens* mediated-transformation system based on shoot nodes as explants. This method, using the tip of a syringe needle, involves gently wounding each node at the axillary position, and introducing *Agrobacterium*, which harbors the vector containing the Agronomically-important genes. The method requires each and every node to be wounded by hand, one at a time. Furthermore, the transformation efficiency rate for this technique is extremely low, 0.71% or less. In other words, the existing method for transformation of Guayule is time consuming, tedious, and inefficient.

Other transformation methods have been attempted with varying degrees of success—transformation is highly species-specific and genotype-dependent. Stated differently, what works well in one species often does not work well, or at all, in another species. Moreover, the species that are amenable to existing transformation techniques are not always those with high commercial value such as latex-producing Guayule.

What is needed, then, is a method of transformation for Guayule that is efficient and economical.

SUMMARY OF THE INVENTION

Applicants have invented a technique for Guayule transformation that is highly efficient and therefore quite economical. Instead of relying on a transformation technique that involves wounding Guayule shoot stock one-at-a-time, the new technique uses pieces of Guayule leaves that can be transformed en masse. Various agronomically important genes can thus be transferred into Guayule plants in large numbers, creating new transgenic lines.

This novel technique produced surprising and unexpected results because previous attempts to use leaf strips for transformation met with highly irregular results, often failing altogether. For example, most attempts to induce organogenesis in leaves using full MS medium and normal light conditions resulted in leaf tissue that browned and withered rapidly. This failure by others has been resolved.

Using *Agrobacterium* and then holding leaf strips in a nutrient matrix under reduced light conditions, the inventors have successfully introduced foreign genes into pieces of Guayule leaves, or explants, which were then grown into plant shoots that eventually grew into healthy, full size plants. Leaf strips provide a major advantage over plant shoots in the transformation process—they typically produce a much higher efficiency rate by a factor of 10 over the prior art (See FIG. 5).

Using this technique, large numbers of Guayule plants can be transformed with agronomically important genes, thus substantially increasing the latex yield of any cultivated Guayule crop.

A major advantage of this invention is that it provides a successful method for conducting Guayule transformation, especially in light of the previous known methods, which are highly inefficient and labor intensive.

A further advantage of this invention is that it allows for large-scale production runs for Guayule transformation, a development with major industrial implications.

Yet another advantage is that the invention will greatly assist the nascent Guayule industry, allowing it to dramatically boost the yield of latex from the Guayule crop.

Still another advantage is that the invention will provide major benefits to the latex-rubber industry in its effort to create a stable domestic supply of hypoallergenic latex rubber.

Still another advantage is that the invention will allow the growing range of Guayule to be extended.

DEFINITIONS

Definitions and concepts, unless specified herein, are those which are found in Nelson and Cox, *Lehninger Principles of Biochemistry* (3d ed. 2000) and/or Alberts, *Molecular Biology of the Cell* ($4^{th}$ ed. 2002).

"Rubber" is a naturally-occurring hydrocarbon polymer of cis-1,4-polyisoprene with 400-50,000 isoprene monomeric units enzymatically linked in a head-to-tail configuration. "Rubber" can also refer to various elastomers such as butadiene (not natural rubber) that possess rubbery properties.

Latex is a suspension of rubber particles.

"Latex Product" is a rubber product that has as starting materials latex.

Guayule is a plant whose scientific name is *Parthenium argentatum* Gray.

G7-11 is a high-yielding, fast-growing Guayule line.

AZ101 is a genetically uniform selection of a naturally occurring hybrid of Guayule, which shows properties of high resistance and hardiness. Moreover, AZ101 is a cross between Guayule line 11591 and a related species, *Parthenium tomentosum*.

"Transforming" or "transformation" is any genetic change brought about by the introduction of exogenous DNA into a cell. Transformation is initiated by the introduction of foreign DNA into embryonic or non-differentiated tissue so that it becomes incorporated into the germ-line (the chromosome) of the individual, and thus is stably inherited in subsequent generations of transgenic organisms.

Organogenesis is the process of formation of specific plant organs involving morphogenesis and differentiation. Once transformation is achieved, organogenesis must be induced, otherwise the plant will die and no new transgenic plant will be obtained.

35S-p is a promoter from cauliflower mosaic virus that is used to drive expression of the BAR gene.

PPT is phosphinothricin which is an analogue of glutamic acid and acts as an inhibitor of glutamine synthesis in plants, thus acting as a herbicide.

The BAR gene codes for PPT acetyltransferase and has been isolated from *S. Hygroscopicus*. It is widely used as a selective marker for the transformation of higher plants (De-Block et. al., 1987, EMBO J., 6:2513-18).

UB3-p is a promoter from potato and is used to drive expression of the GUS gene.

The GUS gene is beta glucuronidase.

GUS staining is a method used to detect whether and where a GUS gene has been expressed inside the cell.

Glufosinate is an herbicide that would ordinarily kill Guayule. The BAR gene confers resistance to glufosinate, permitting a plant that has the BAR gene to survive exposure to glufosinate. Coupling BAR with the GUS gene, attempting to insert said genes into Guayule, and then treating the resulting plant with glufosinate will confirm whether the genes were successfully transferred, whether transformation was successful. Glufosinate is an example of "selectable medium," and herbicides used for the same or similar purpose are known as "selectable media."

Micropropagation or proliferation is the process by which multiple, genetically identical shoots or plants are produced.

"Plantlets" are small, complete plants.

"Explants" are pieces of plants.

"Controlled light conditions" means controlling the intensity and duration of light exposure in order to allow leaf tissue to produce shoots after being cut and infected by *Agrobacterium*. Examples of these are provided in the specification.

"Reduced light intensity" is defined as cold white fluorescent light, <15 μmol m$^{-2}$ s$^{-1}$ "Low light intensity" is defined as cold white fluorescent light, <5 μmol m$^{-2}$ s$^{-1}$ "Bright light intensity" is defined as cold white fluorescent light, ≥50 μmol m$^{-2}$ s$^{-1}$ "*Agrobacterium*" refers to small motile bacterial rods that can reduce nitrates and cause galls on plant stems. The *Agrobacterium* referred to herein has been modified by removing the T-DNA which carries the tumor gene. It is identified as the EHA101 *Agrobacterium*. It is a binary vector, pND4, with a backbone of pPZP200 and a T-DNA containing a BAR gene driven by a double 35S promoter and a GUS-intron gene driven by a potato ubiquitin promoter. The vector pND4 has been transformed into a EHA101 to produce pND4-EHA101.

"MSBN" is a nutrient culture medium comprised of MS basic medium plus BA and NAA. "MS" refers to the standard medium as described by Murashige and Skoog. BA is 6-benzyl amino purine, a cytokinin. NAA is α-naphthalene acetic acid.

"MSB2 TG1" is MS basic medium plus 2 mg/l BA and 400 mg/l timentin and 1 mg/l glufosinate.

MSB1TG 0.6 is MS basic medium plus 1 mg/l BA and 200 mg/l timentin and 0.6 mg/l glufosinate.

"Rooting medium" is defined as ½ MS 0.1 mg/l IBA 0.5 mg/l glufosinate. IBA is indol butyric acid.

pND4 is a binary vector containing 35s promoter-BAR gene and ubiquiton-3-promoter-GUS gene.

DETAILED DESCRIPTION OF THE INVENTION

Successful transformation of Guayule plants has been achieved through a technique which combines use of leaf discs or strips soaked in Agrobacteria containing a target gene, controlled light conditions, and a unique blend of culture/nutrient media.

Agrobacteria-mediated transformation has been used with broad leaf plants. The standard technique involves inserting a target gene into a plasmid, transferring the plasmid into Agrobacteria, and then exposing the plant to be transformed to the Agro containing the target gene. This is a sensitive process, however, because it involves infecting the host plant with what is in effect a foreign agent. Plants that have been infected with Agrobacteria in an attempt to transform them often weaken and die because of the infection. In other words, exposing a plant to *Agrobacterium* injures the plant, often fatally.

A method to stabilize and "nurse" the plant back to health is therefore critical, and the process described herein is just such a method. By applying this technique, it is possible to slow the metabolism and cellular processes of the plant, giving it time to heal and overcome the infection. It has been discovered that the metabolism and cellular processes of Guayule can in fact be slowed by using reduced light conditions before transformation as well as during the transformation and micropropagation processes. These reduced light conditions, which will be expanded upon below, are to be considered in relation to "bright light" conditions found in a controlled, growth room environment which is equivalent to cold white fluorescent light with an intensity of ≥50 μmol m$^{-2}$ s$^{-1}$.

Figure 3:
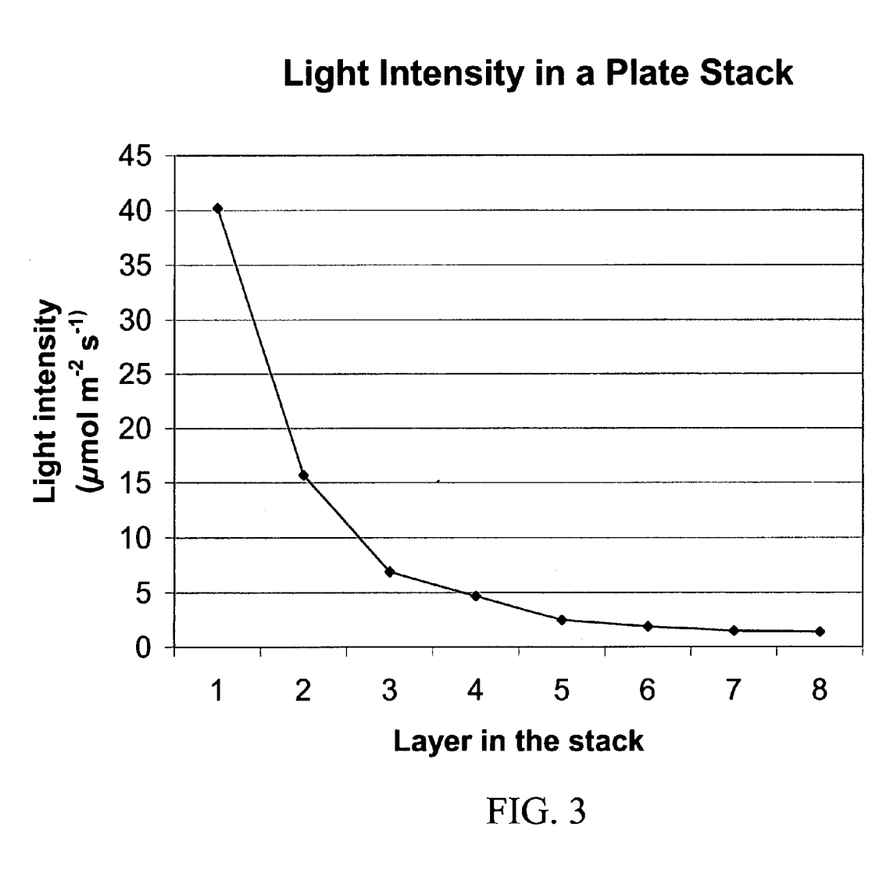
FIG. 3 is a graph showing the relationship between light intensity and the layer at which plantlet samples were held on a rack. Samples held on lower levels received less light than those held on higher levels, closer to the light source.
Figure 4:
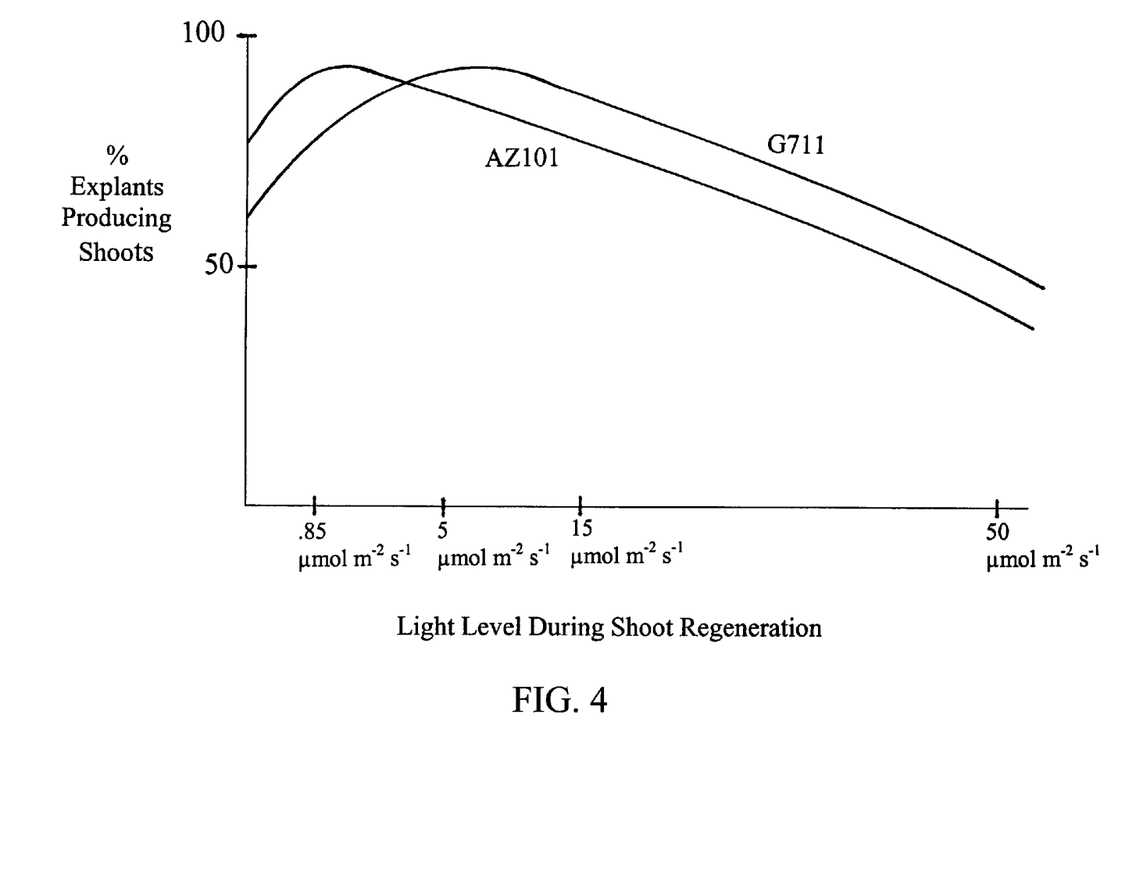
FIG. 4 shows the relationship between light intensity (level) and the success rate for shoot regeneration after transformation of Guayule lines G7-11 and AZ 101.

This phenomenon was first discovered during experiments where it was noted that certain plants that had just been infected with Agro and which were being held on lower racks in a growing chamber and therefore receiving less light, appeared to be doing better and growing more rapidly than plants held on the upper levels and therefore receiving relatively more light. See FIG. 3.

The method begins with a Guayule line that has been grown in sterile culture. Since Guayule is becoming increasingly more important as a source of industrial rubber products, this technique obviously will be useful to those wishing to improve Guayule lines with an eye toward boosting yield and extending range. At any rate, the starting-material plants must be mature enough to provide well-developed leaf material, but not so old that their overall ability to recover is impaired. Plants up to 35 days old are good candidates but those older than 40 days appear to be less than optimum. Leaves taken from these plants will provide the starting materials for the procedure.

Leaves are harvested from the growing plants and are cut into pieces or strips, using a sterile cutting device such as a sterile surgeon's blade. As an aside, it should be emphasized that all supplies and media should be sterilized and all procedures are best done inside a laminar flow hood or other sterile cabinet in order to prevent contamination. At any rate, the leaf strips or discs may vary in size and shape, although they are preferentially cut into approximately 5-8 mm strips. One variant of this procedure involves holding the cut leaf strips in controlled light conditions for a period of 0-21 days before exposing them to Agrobacteria, while another variant does not include this "pre-culture" holding period. This will be expanded upon in the sample assay and examples section below.

The transformation step begins with the preparation of the vector containing the gene of interest. This is ordinarily done by placing the gene of interest along with the appropriate promoter and terminator regions into a plasmid which is used to transform a culture of Agrobacteria. This culture will ordinarily be held in a container, set aside in preparation for receiving cut leaf strips. Various genes of interest can be introduced in this fashion. The examples section below shows how the technique has been used with the BAR and GUS genes, but the technique is also effective with other genes.

The leaf strips (explants) are soaked in the *Agrobacterium* culture in order to introduce the target gene into the explants which will hopefully become a new Guayule line. It is usually sufficient to soak the leaf strips in this solution for approximately 10 minutes, stirring occasionally. The leaf strips are then removed from the *Agrobacterium* culture, blotted with sterile filter paper, and transferred to a Petri dish or other suitable laboratory ware which contains suitable nutrient media. At this stage, a nutrient medium comprised of 1/10$^{th}$ MSBN is a good choice. The leaf strips and *Agrobacterium* are co-cultured in this condition for 2-3 days and kept in the dark.

Following the 2-3 day co-culture period, reduced light conditions are applied. The range of reduced light/low light conditions are further elaborated upon in the Examples and Assays section below. It should be noted however, that full "bright light" in a growth room is in the range of at least 50 μmol m$^{-2}$ s$^{-1}$, and "reduced light" will generally be in the range of <15 μmol m$^{-2}$ s$^{-1}$ and may include periods of darkness. The leaf strips are held in these reduced light conditions for approximately 3-4 weeks in order to help them heal from the exposure to agro and to hopefully induce proliferation. During this period, it is also useful to apply a nutrient media comprised of ½ MSB2 TG1, and to replenish it approximately every 10-14 days.

After approximately 4 weeks (but sometimes as late as 8 weeks), individual leaves will produce shoots. Root stock can then be attached to the shoots to produce plantlets (small, complete plants).

The proliferation and micropropagation process described herein results in a higher percentage of explants surviving the agrobacteria exposure, particularly compared to other transformation techniques that use leaf strips as starting materials. For example, the standard shoot transformation technique (as described in Pan) has an efficiency rate of only about 0.7%, while the technique described herein shows an efficiency rate of between 5-9.5%. (See FIG. 5). Using this transformation technique, large numbers of transgenic plants can more easily be created to expand the climatic growth range of the plant, plant size, and the amount of rubber produced from each plant.

Figure 1:
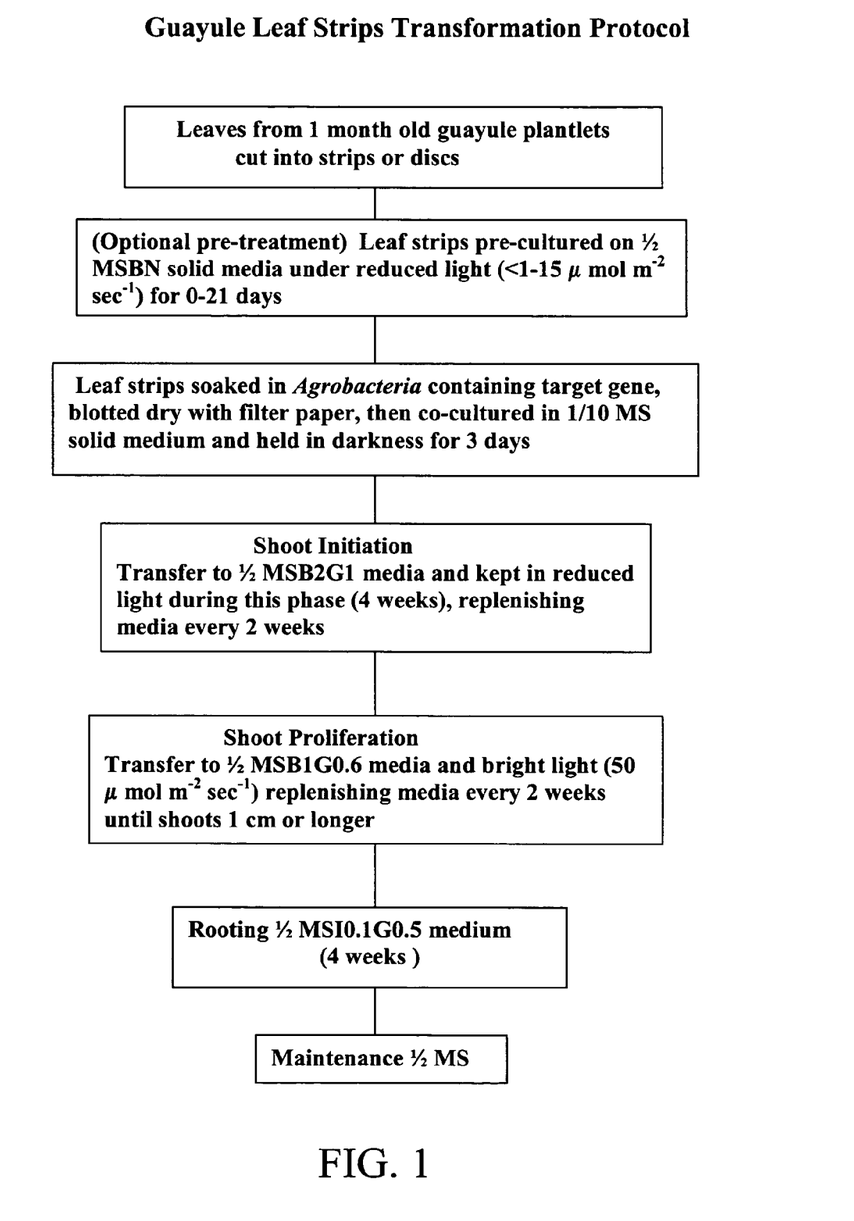
FIG. 1 shows a flow chart, outlining the steps of the Guayule leaf strip transformation protocol.
Figure 2:
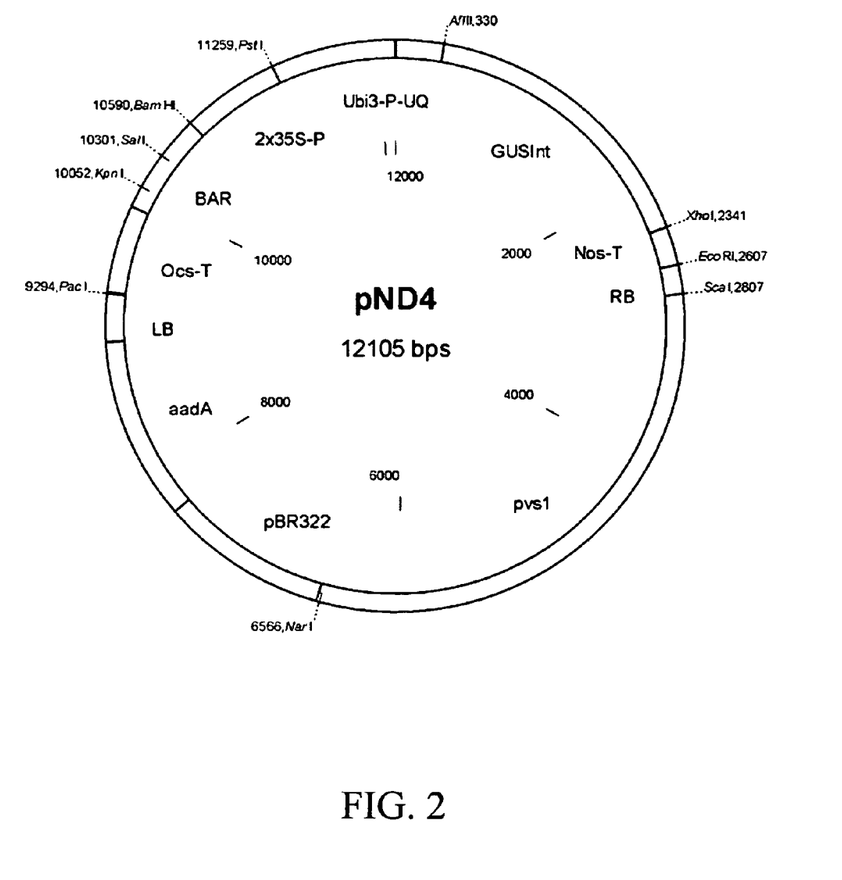
FIG. 2 shows a gene map of a plasmid, pND4. Other plasmids may also be used for Guayule transformation, depending upon need and availability. This particular plasmid map shows the relative position of the following: potato ubiquitin-3 promoter plus the first ubiquitin coding sequence (Ubi3-P-UQ); GUS gene with an intron (GUSInt); Nopline synthase gene terminator (Nos-T); Spectinomycin resistant gene (aadA); Octopine synthase gene terminator (Ocs-T); Herbicide glufosinate resistant gene (BAR); and the double 35S promoter (2×35-P). The plasma backbone is depicted in the lower half of the figure, between the left border (LB) and the right border (RB).

The following examples and assays will demonstrate the range and optimum conditions to be used with the technique. A summary of the transformation protocol can also be found in a flowchart at FIG. 1.

EXAMPLES AND REPRESENTATIVE ASSAYS

As illustrative examples, a 35S promoter driven BAR gene and a ubiquitin-3 promoter driven GUS gene (with intron) were successfully introduced into Guayule lines using the method described herein.

Preparation and Maintenance of Guayule Lines

Transformation of Guayule ordinarily requires the maintenance of healthy and stable Guayule plants in order to provide raw materials. Various lines of Guayule will provide suitable starting materials. For these experiments, cultures of Guayule lines G7-11 and AZ101Cl were used. These were established and maintained as described in Castillón and Cornish (2000). The method also has proved suitable for line N6-5 and is expected to work in all Guayule germplasm. G7-11 and AZ101CL were targeted because they are at the center of the nascent Guayule latex rubber industry. G7-11 is representative of the rapidly-growing high yield lines released by the USDA and University of Arizona plant breeding program and is grown commercially under the name AZ2. AZ101 is a low yielding but very robust and resistant large biomass line that would be an excellent commercial candidate once its rubber yield has been boosted by genetic engineering. In addition, other advanced lines, including but not limited to AZ1, AZ3, AZ4, AZ5 and AZ6 would be suitable for genetic manipulation using this method.

Preparation of the *Agrobacterium* and *Agrobacterium* Glycerol Stock

A single colony of Agro on LB+Kan75 mg/l Spec100 mg/l Chlo25 mg/l plate was used for this procedure. Other antibiotics might also be used.

Suspensions of *Agrobacterium* EHA101 harboring the pND4 binary vector were prepared by inoculating 10 ml LB medium with an antibiotic such as Spectinomycin (200 mg/l) or Rifampcyin (20 mg/l) and adding 100 µl long term glycerol stock in a 50 ml Falcon tube, and shaking overnight at 28° C. The suspension then was centrifuged for 15 min at 1600 g at room temperature. The supernatant was discarded and the pellet was re-suspended in 20 ml of Inoculation Solution (⅒ MS salts plus BA 4 mg/L, NAA 0.5 mg/L, Glucose 10 g, Acetosyringon 200 µM, Pluronic F68 10%, pH 5.4).

Using sterile technique in a laminar flow hood, the Agro LB+Kan 25 Spec100 Chlo75 plate was introduced into a sterile culture tube containing 10 ml of LB+Kan75 Spec100 Chlo25 broth. The culture tube was then placed into an incubator set at 25° C. and centrifuged at 225 rpm overnight. The cultures were kept at 25-28° C. in order to reduce the likelihood of the Agro rejecting the plasmid. Agro glycerol stock was also prepared from the Agro culture.

Preparation and Effect of Culture Media

When leaf strips were cultured on MSB2 medium, which has been the standard culture medium (Pan et al., 1996), they turned brown and withered within 2 weeks. Modifications of the media, such as changing the BA concentration from 1-8 mg/L, adding 20-160 mg/L ascorbic acid or 1-8 mg/L $AgNO_3$, or replacing sucrose with glucose, did not significantly change explant health. The same results were obtained when using leaf strips from two week old and 1 month old plantlets.

The standard MS medium (Murashige and Skoog, 1962) was modified by diluting it to half strength (½ MS) and adding 5 g/l $KNO_3$ (total $KNO_3$ 5.95 g/l) with a pH 5.8. The increased $KNO_3$ and reduced $NH_4NO_3$ improved leaf tissue growth. The use of potassium nitrate and ammonium nitrate produced unexpected results because ammonium is not a good nitrogen source in this case—nitrate worked better.

The culture medium was also adjusted once green shoots emerged from the inoculated leaf strips—once such shoots appeared, the explants were transferred to ½MSB1TG0.6 medium (½ MSB1 plus Timentin 200 mg/L, Glufosinate 0.6 mg/L) for elongation and further selection. Green shoots 10 mm and longer were transferred to ½MSI0.1TG0.5 medium (½MSI0.1 plus Timentin 200 mg/L and Glufosinate 0.5 mg/L) for rooting. Shoot tips of the rooted plantlets were subcultured in ½MS medium.

It was also noted that Guayule leaf tissue that grew on ½MSB2 medium had less wounding response than that on MSB2 medium.

Figure 6:
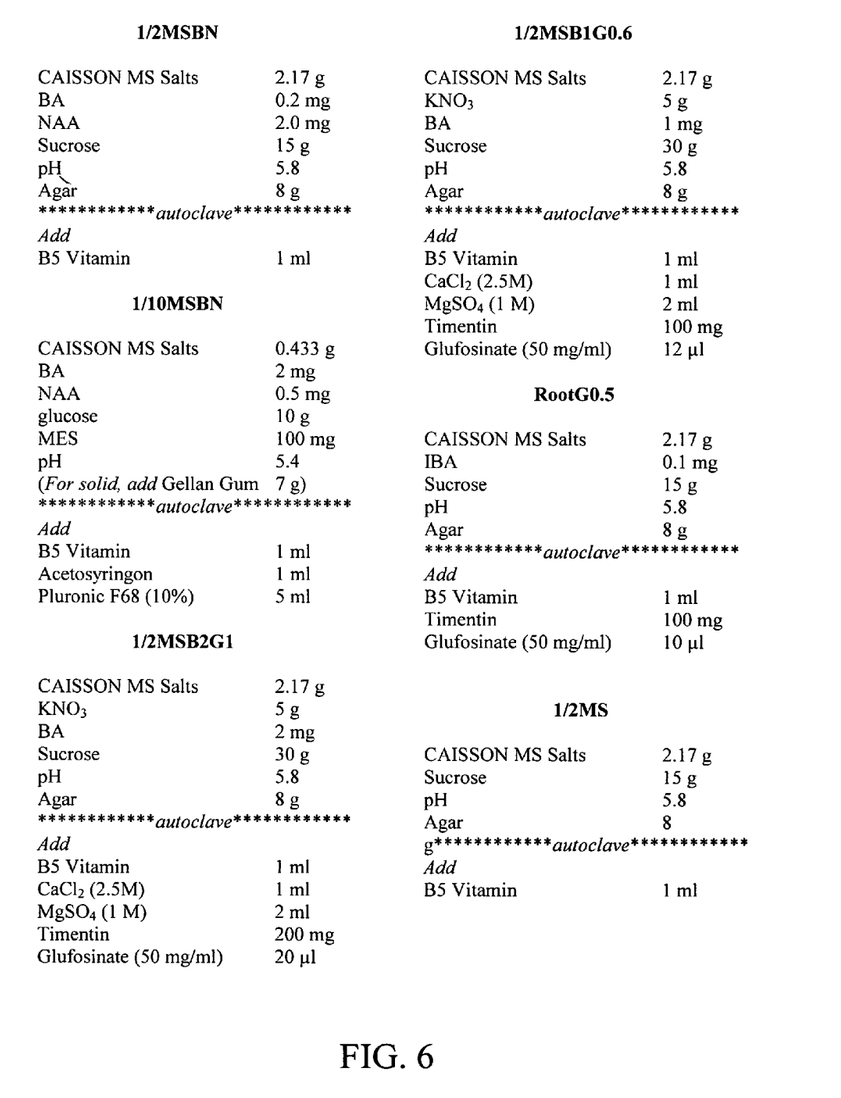
FIG. 6 shows the various formulations of nutrient media used throughout the disclosed experiments.

Therefore, it was apparent that the selection of culture media was important. The particular formulation combinations that were used in these experiments, along with low-light conditions, produced unexpected results. Various formulations are listed in FIG. 6.

Transformation Through Use of Leaf Tissue and Low Light

The transformation step is where the foreign genes were actually transferred into the target plant, in effect "transforming" that plant's genetic identity. In this example, BAR and GUS genes were transferred into the subject Guayule lines, in effect creating transgenic plants. The vector used to transfer the gene was the pND4 plasmid, as described above. The starting materials for this transformation were leaf strips harvested from Guayule plants that were approximately 30-35 days old. Leaf strips were taken from Guayule lines G7-11 and AZ-101, and two separate variants of the procedure were used, described below.

Procedure A

One-month old Guayule plantlets, cultured in ½ MS medium, were used to prepare the leaf strips. It was important to use plantlets that were no older than 35 days since older Guayule plant tissue progressively loses its ability to recover from the wounding inflicted by the Agro. Using sterile technique, the leaves were cut into approximately 8 mm strips. The size and shape of the leaf strips was not critical, with the dominant factor simply being ease of handling.

The leaf strips were transferred to ½ MSBN medium where they were pre-cultured in reduced light (<15 $\mu mol\ m^{-2}\ s^{-1}$) for periods of 0-21 days, depending on the particular assay.

Following the pre-culture period, the leaf strips were then soaked in the *Agrobacterium* suspension containing the target gene, prepared as described above, at room temperature for 10 min. The soaked leaf strips were then blotted with filter paper and placed in 1/10 MSBN medium (Inoculation Solution plus Agar 9 g/L) and held in the dark for 3 days of co-cultivation.

After 3 days of co-cultivation in the dark, the leaf strips were subjected to low light conditions and transferred to ½ MSB2TG1 medium (½ MSB2 plus Timentin 400 mg/L, Glufosinate 1 mg/L) for shoot initiation and selection of transformants. The leaf strips were transferred to fresh medium every 2 weeks, it being necessary to replace and replenish the media because of toxic byproducts generated by the natural metabolic processes of Guayule. The controlled (low) light conditions ranged from darkness to 15 $\mu mol\ m^{-2}\ s^{-1}$, depending on the assay. Guayule line AZ101 responded best (showed the highest transformation rate) at 0.85 $\mu mol\ m^{-2}\ s^{-1}$, and G7-11 did best when held at 5 $\mu mol\ m^{-2}\ s^{-1}$.

Following shoot initiation, the explants were transferred to a new medium, ½ MSB2G1, and brought into bright light (50 $\mu mol\ m^{-2}\ s^{-1}$) for shoot proliferation. This media formulation was replaced every 2 weeks until the shoots were approximately 1 cm long or longer. Rooting was then conducted using standard techniques.

Procedure B

The following materials were assembled: Guayule plants, 10 ml LB+Kan25 Spec75 Chlo100 broth cultures of the Agro, 50 ml Falcon tube, sterile filter paper, petri dishes—100×15 mm, 150×15 mm, scalpel, forceps, sharpie, incubator, centrifuge, and growth room capable of maintaining 25° C. and maintaining lighting conditions in the range of <1 $\mu mol\ m^{-2}\ s^{-1}$ to ≥50 $\mu mol\ m^{-2}\ s^{-1}$. The following media were also prepared: 1/10 MSBN Inoculation Solution, 1/10 MSBN (plates), ½ MSB2T (plates), ½ MSB2TK50 (plates), ½ MSB1TK50 (Magenta boxes), and ½ MSI0.1K25 (Magenta boxes).

Using sterile technique, leaves from one month old Guayule plants were cut into 3-4 mm wide strips and immediately placed into a Petri dish containing the Agro solution. It was important to select leaves that were not wrinkled, discolored or curled upward, since leaves in that condition are likely to be in poor health—in other words, such leaf tissue was not a good candidate for the transformation experiments. The leaf strips were soaked in the Agro solution for 10 minutes, using a rocker to ensure contact between the Agro and the leaf strips. The Agro solution was then drained from the Petri dish.

Using forceps, the leaf strips were removed from the Petri dish and placed onto sterile filter paper. They were then blotted using another piece of filter paper, a process which removed any excess Agro from the leaf strips.

The leaf strips were next placed on 1/10 MSBN plates and placed in a growth room set at 25° C. and held in darkness for a period of 3 days. Darkness was achieved by using a light-tight box with a lid, or by covering the plates completely with foil.

After three days of culturing in darkness, the leaf strips were transferred to ½ MSB2T medium (plates) and placed in a growth room set at 25° C. and were subjected to low light conditions for approximately the next four weeks or until shoot initiation occurred. The low light conditions included alternating periods of darkness and light with an intensity ≤15 $\mu mol\ m^{-2}\ s^{-1}$. Various periods were used, depending on the particular assay. The best results (highest transformation rates) were achieved by subjecting to AZ101 to light at 0.85 $\mu mol\ m^{-2}\ s^{-1}$, and G7-11 to light at 5 $\mu mol\ m^{-2}\ s^{-1}$. The culture medium was also replaced every two weeks.

After green shoots appeared, the leaf strips were transferred to ½ MSB1TK50 medium (Magenta Boxes) and placed in a growth room set at 25° C., in bright lighting, ≥50 $\mu mol\ m^{-2}\ s^{-1}$, to allow for shoot elongation and proliferation. When the shoots reached approximately 1 cm in length, they were transferred to Sorba-rods in ½ MSI0.1K25 Solution and placed into a growth room set at 25° C., in bright lighting, 50 $\mu l\ mol\ m^{-2}\ s^{-1}$. Sorba-rods, which are made of cellulose, prevent agar from sticking to root members (which might damage root hairs) and thereby are an aid when the plantlets are transferred from media to soil. Use of sorba rods also helps prevent conditions which can lead to harmful bacteria colonizing the media and thereby infecting the plantlets, possibly causing them harm.

Rooting was done by standard techniques and as described above.

Lighting Conditions

In bright light (≥50 $\mu mol\ m^{-2}\ s^{-1}$), Guayule explants undergoing organogenesis turn brown, wither and die, probably because Guayule is a plant rich in secondary metabolites, many of which are toxic such as the phenolics. The reduced light used in these experiments apparently suppressed metabolism, or at least the production of some of the toxic metabolites, which evidently allowed the leaf strips to recover from the *Agrobacterium* infection.

Figure 5:
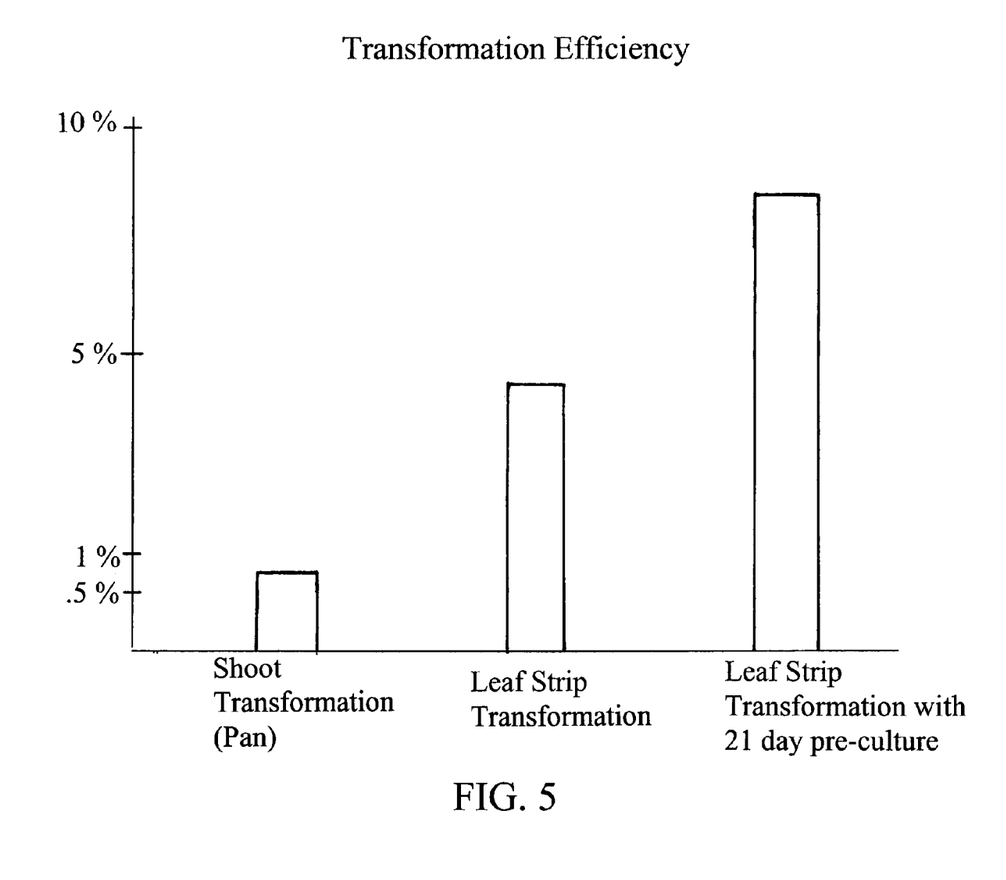
FIG. 5 shows the transformation efficiency rates for shoot transformation as described by Pan, and for leaf strip transformation both with and without a 21 day pre-culture step which involves holding the leaf strips in reduced light before exposure to Agrobacteria containing a target gene.

Low light intensity and use of leaf strips operated to considerably improve transformation efficiency rates compared to standard transformation techniques which involve shoot (not leaf) transformation (FIG. 5). This finding was totally unexpected because it was commonly understood that leaf tissue must have abundant light for regeneration.

Light intensity experiments ranged from keeping the leaf strips in total darkness to exposing them to various degrees of reduced light at different stages of development. For Guayule line AZ101, the range tested was from total darkness to 50 $\mu mol\ m^{-2}\ s^{-1}$, with the optimum being at 0.85 $\mu mol\ m^{-2}\ s^{-1}$. For Guayule line G711, the range tested was from total darkness to 50 $\mu mol\ m^{-2}\ s^{-1}$, with the optimum being at 5.0 $\mu mol\ m^{-2}\ s^{-1}$. Holding leaf strips in darkness for 3 days following exposure to Agro, followed by a nursing stage of approximately 4 weeks of exposure to low light resulted in a transformation efficiency rate of approximately 5%. The efficiency rate can be boosted to nearly 10% if the leaf strips are held in reduced light and co-cultured for periods of 0-21 days (depending on the assay) prior to exposure to Agro.

Low light intensity was known to be essential for somatic embryogenesis, probably because natural embryogenesis occurs inside the ovary. Organogenesis, however, occurs at the surface of explants where it is exposed to the environment.

Until now, it was understood that high light intensity (bright light) was necessary for organogenesis, particularly when using leaf tissue. Achieving success in using reduced light conditions for inducing organogenesis from leaf tissue, therefore, is unexpected.

Experiments Confirming Transformation

Various experiments were conducted to confirm that transformation had occurred. For example, histochemical staining was used to detect GUS activity as described by Jefferson and Wilson, 1991. Endogenous GUS activity was not detected in leaf segments from non-transformed control plants. Out of 200 explants subjected to the technique described herein, transformation efficiency was equal to or greater than 4-5%. This is a significant improvement over the shoot node method (<1%) described in Pan, which up until now has been the dominant technique used for transformation.

The experimental plants were also tested for herbicide/glufosinate resistance. This was achieved by soaking both non-transformed and transformed leaf disks in 1 mg/L glufosinate. After 1 week, the leaf discs from the non-transformed control plant turned yellow, while the leaf discs from transformed plantlets remained green. This was evidence that these plants are glufosinate resistant, thus confirming that the target gene had in fact been transferred.

PCR was also conducted to confirm that transformation had occurred. Plant DNA was prepared using the DNAeasy Plant Mini Kit (QIAGEN). The primer GUS_SnaBI (GCC GGG AAA AGT GTA CGT AAG TTT C) (SEQ ID NO:1) was used as a forward primer and GUS_BstBI (GCC CGC TTC GAA ACC AAT GCC) (SEQ ID NO:2) was used as a reverse primer. For each PCR, the amount DNA used was 20 ng for plasmid as positive control and 250 ng for each plantlet. The reaction mixture contained 0.4 mM NTPs, 0.25 mM $MgCl_2$, 1 μM of each primer, Taq polymerase buffer and 5 unit of Taq polymerase. After heating the samples to 94° C. for 3 min, the reaction proceeded with 30 cycles of 94° C. for 30 sec, 62° C. for 30 sec and 72° C. for 60 sec. A final elongation step was carried out at 72° C. for 10 min. PCR products were separated by electrophoresis on 0.8% (wt/vol) agarose-ethidium bromide gels. This PCR product showed that the GUS gene was present in the transformed plant genome.

What is claimed is:

1. A method for transforming *Parthenium argentum* (Guayule) with a target gene, comprised of the steps of:
   a. dipping and saturating leaf strips of Guayule, previously grown in sterile culture, in a solution of *Agrobacterium* which has been transformed with a vector containing a target gene; and
   b. introducing said leaf strips to a nutrient subculture and to controlled light conditions which are comprised of alternating periods of darkness and fluorescent light maintained at <15 μmol $m^{-2}$ $s^{-1}$ intensity, and maintaining said leaf strips under said controlled light conditions in said nutrient subculture until shoot formation occurs; optionally, with subsequent root formation, thus producing transformed plantlets of Guayule.

2. The method of claim 1, wherein the controlled light conditions are comprised of alternating periods of darkness and fluorescent light maintained at between 0-5 μmol $m^{-2}$ $s^{-1}$ intensity.

3. A method of transforming Parthenium argentatum (Guayule) with a target gene, comprised of the steps of:
   a. dipping and soaking leaf strips of Guayule, previously grown in sterile culture, in a solution of *Agrobacterium* which has been transformed with a target gene;
   b. introducing said leaf strips to selectable media; and
   c. slowing the metabolism of said leaf strips held in a nutrient matrix until shoot formation occurs by exposing the nutrient containing the leaf strips to alternating periods of darkness and light that is <15 μmol $m^{-2}$ $s^{-1}$ intensity; optionally, with subsequent root formation, thus creating transformed plantlets.

4. The method of claim 3 wherein the metabolism is slowed by exposure to and maintenance of controlled light conditions.

5. A method for transforming *Parthenium argentatum* (Guayule) with a target gene, comprised of the steps of:
   a. preparing leaf strips from Guayule plants previously grown in sterile culture, and holding said leaf strips in reduced light conditions defined as alternating periods of darkness and exposure to white fluorescent light with an intensity of <15 μmol $m^{-2}$ $s^-$ for at least 3 days;

SEQUENCE LISTING

<160> NUMBER OF SEQ ID NOS: 2

<210> SEQ ID NO 1
<211> LENGTH: 25
<212> TYPE: DNA
<213> ORGANISM: Artificial
<220> FEATURE:
<223> OTHER INFORMATION: GUS_SnaBI was used as a forward primer

<400> SEQUENCE: 1
gccgggaaaa gtgtacgtaa gtttc                                         25

<210> SEQ ID NO 2
<211> LENGTH: 21
<212> TYPE: DNA
<213> ORGANISM: Artificial
<220> FEATURE:
<223> OTHER INFORMATION: GUS_BstBI was used as a reverse primer

<400> SEQUENCE: 2
gcccgcttcg aaaccaatgc c                                             21 b. preparing *Agrobacterium* liquid suspension containing a binary vector with at least one target gene in its T-DNA;
c. soaking said leaf strips in the Agrobacterium suspension;
d. introducing said leaf strips to a selectable medium;
e. transferring said leaf strips into a nutrient culture, and exposing the leaf strips to controlled light conditions until proliferation occurs; optionally, with subsequent shoot and root formation, thus producing a colony of transformed Guayule plants.

6. The method of claim 5, wherein the controlled light conditions are further defined as alternating periods of darkness and exposure to white fluorescent light with an intensity of <5 $\mu mol\ m^{-2}\ s^{-1}$.

* * * * *